United States Patent [19]

Okazaki

[11] Patent Number: 5,311,869

[45] Date of Patent: * May 17, 1994

[54] METHOD AND APPARATUS FOR ULTRASONIC WAVE TREATMENT IN WHICH MEDICAL PROGRESS MAY BE EVALUATED

[75] Inventor: Kiyoshi Okazaki, Takanezawa, Japan

[73] Assignee: Kabushiki Kaisha Toshiba, Kawasaki, Japan

[ * ] Notice: The portion of the term of this patent subsequent to Sep. 29, 2009 has been disclaimed.

[21] Appl. No.: 673,335

[22] Filed: Mar. 22, 1991

[30] Foreign Application Priority Data

Mar. 24, 1990 [JP] Japan .................. 2-074394
Sep. 10, 1990 [JP] Japan .................. 2-237132

[51] Int. Cl.⁵ .................. A61B 17/22
[52] U.S. Cl. .................. 128/660.03; 601/4
[58] Field of Search .................. 128/660.01, 660.03, 128/660.07, 804, 24 EL; 606/127, 128

[56] References Cited

U.S. PATENT DOCUMENTS

| Re. 33,590 | 5/1991 | Dory . | |
| 3,828,770 | 8/1974 | Kuris | 128/62 |
| 4,191,189 | 3/1980 | Barkan | 128/328 |
| 4,617,931 | 10/1986 | Dory | 128/328 |
| 4,658,828 | 4/1987 | Dory | 128/660 |
| 4,696,425 | 9/1987 | Landes . | |
| 4,741,008 | 4/1988 | Franke | 128/24 EL |
| 4,811,725 | 5/1989 | Grasser | 128/24 EL |
| 4,958,639 | 9/1990 | Uchiyama et al. | 128/660.03 |
| 4,976,255 | 12/1990 | Reichenberger et al. | 128/24 |
| 4,986,275 | 1/1991 | Ishida et al. | 128/660.03 |
| 5,014,686 | 5/1991 | Schafer | 128/24 EL |
| 5,031,626 | 7/1991 | Hassler et al. | 128/660.03 |
| 5,080,101 | 1/1992 | Dory . | |
| 5,080,102 | 1/1992 | Dory . | |
| 5,150,713 | 9/1992 | Okazaki | 128/660.03 |

FOREIGN PATENT DOCUMENTS

| 339693 | 3/1985 | European Pat. Off. . |
| 355178 | 8/1988 | European Pat. Off. . |
| 414209 | 8/1990 | European Pat. Off. . |
| 3215748 | 11/1983 | Fed. Rep. of Germany . |
| 3736733 | 5/1988 | Fed. Rep. of Germany . |
| 1-129845 | 5/1989 | Japan . |

Primary Examiner—Lee S. Cohen
Assistant Examiner—Brian L. Casler
Attorney, Agent, or Firm—Foley & Lardner

[57] ABSTRACT

A method and an apparatus for an ultrasonic wave medical treatment in which it is possible to cheek the effect of the treatment in the course of the treatment, while executing the treatment process efficiently. In the apparatus, an entire ultrasonic wave medical treatment process is divided into a plurality of sections; a total number of ultrasonic wave irradiations for the entire ultrasonic wave medical treatment process and a sectional number of ultrasonic wave irradiations for each of the plurality of sections are set; and ultrasonic waves are irradiated on a treatment target for the total number of times, such that the ultrasonic waves are irradiated for the sectional number of times for each of the plurality of sections and then the ultrasonic waves radiation pauses before the ultrasonic wave irradiation for a subsequent one of the plurality of sections is executed.

16 Claims, 11 Drawing Sheets

TREATMENT PLAN MENU

IMAGE RECORDING    START SHOT NO.=0
    STOP SHOT NO.=2000
    STEP SHOT NO.=500

SHOCK WAVE IRRADIATION    START POWER=20%
    STOP POWER=90%
    STEP POWER=10%
    POWER STEP SHOT NO.=50
    PAUSE SHOT NO.=200

METHOD AND APPARATUS FOR ULTRASONIC WAVE TREATMENT IN WHICH MEDICAL PROGRESS MAY BE EVALUATED

BACKGROUND OF THE INVENTION

1. Field of the Invention

The present invention relates to a method and an apparatus for an ultrasonic wave medical treatment such as a shock wave treatment in which a treatment target such as a cancer tissue or calculus in a patient is destroyed by utilizing a concentrated energy of ultrasonic shock waves, or an ultrasonic thermal treatment in which a treatment target such as a cancer tissue is destroyed by using a thermal effect of continuous ultrasonic waves.

2. Description of the Background Art

Recent progress have been made on a shock wave medical treatment apparatus for destroying a treatment target such as a cancer tissue or calculus in a patient by utilizing a concentrated energy of ultrasonic shock waves.

An example of a recently developed shock wave medical treatment apparatus is disclosed in Japanese Patent Application No. 62-290158 (1987) by the present inventor, which will now be described with reference to FIG. 1.

This shock wave medical treatment apparatus of FIG. 1 comprises: a shock wave applicator 17 including a shock wave transducer 15 for transmitting ultrasonic shock waves, and an ultrasonic wave transducer 16 for transmitting imaging ultrasonic waves to carry out a B mode scanning (tomographic imaging) and receiving echo signals resulting from the B mode scanning; a pulser 18 for providing pulse signals to drive the shock wave transducer 15; a transmitter and receiver circuit 19 for providing pulse signals to drive the ultrasonic wave transducer 16, and collecting the echo signals received by the ultrasonic wave transducer 16; a signal processor circuit 20 for converting the echo signals collected by the transmitter and receiver circuit 19 into video signals by applying the amplitude detected; a signal converter circuit 21, such as a digital scan converter, for performing signal conversion on the video signals obtained from the signal processor circuit 20; a CPU 22 for controlling the operation of each element of the apparatus; a timing controller 23 for controlling the process timing of the pulser 18 and the transmitter and receiver circuit 19; a display unit 27 for displaying a fan shaped acoustic region 42 imaged by the ultrasonic wave transducer 16 and images of the body surface, organ or calculus along with a focal point marker 26 indicating a focal point of the ultrasonic shock wave transmitted by the shock wave transducer 15; a pulse generation switch 29 connected to the CPU 22 for setting the timings for generating the pulse signals to be given from the pulser 18 to the shock wave transducer 15; and a position controller 30 for adjusting the relative position of the shock wave transducer 15 and the ultrasonic wave transducer 16.

Referring now to FIG. 2, details of the shock wave applicator 17 will be described.

This shock wave applicator 17 comprises: the shock wave transducer 15 for transmitting the ultrasonic shock waves focused to a focal point 41a located inside a patient 32; a water bag 33 containing water which is provided on a shock wave transmitting side 15a of the shock wave transducer 15 and which functions as an acoustic coupler; and the ultrasonic wave transducer 16 for transmitting the imaging ultrasonic waves to carry out the B mode scanning and receiving echo signals resulting from the B mode scanning at a transmitting and receiving surface 16a, which is located within a shock wave region 41 between the shock wave transmitting side 15a of the shock wave transducer 15 and the focal point 41a of the ultrasonic shock wave, and which forms the acoustic field 42 including the focal point 41a.

In further detail, the shock wave transducer 15 has a concave oscillator (not shown) of a constant curvature, and at a center of this shock wave transducer 15 the ultrasonic wave transducer 16 is attached through a supporting and driving unit 36 which support the ultrasonic wave transducer 16 with respect to the shock wave transducer 15, and changes the relative position of the ultrasonic wave transducer 16 in a direction of the arrow B with respect to the shock wave transducer 15, according to the control signals from the position controller 30. This can be furnished for example by providing a rack member on a side of the ultrasonic transducer 16 and a pinion gear connected to a motor in the supporting and driving unit 36, where a rotation angle of the motor is controlled according to the control signals from the position controller 30 (FIG. 10)

The water bag 33 located on the shock wave transmitting side 15a of the shock wave transducer 15 has an approximately cylindrical shape with a bottom surface of approximately the same radius as the shock wave transducer 15, formed by a side bellows 33 which can be extended or contracted within a prescribed angle range from the direction of the arrow B and a bottom side 37 made of a thin film having approximately the same acoustic impedance as the water.

In this shock wave medical treatment apparatus, a renal calculus 39 in a kidney 38 of the patient 32 can be treated as follows.

First, the shock wave applicator 17 is positioned over the patient 32 such that the bottom side 37 of the water bag 33 makes a contact with a surface 32S of the patient over the kidney 38. Then, by using the ultrasonic wave transducer 16, the tomographic image of the patient 32 is obtained on the display unit 27. Here, the transmitting and receiving surface 16a of the ultrasonic wave transducer 16 also makes a contact with the surface 32S, so that a clear tomographic image unaffected by the bottom side 37 of the water bag 33 and the water can be obtained.

Next, when the image of the kidney 38 is obtained on the display unit 27, the renal calculus 39 is searched on the display unit 27. Here, the display unit 27 also displays the shock wave region 41 and the focal point marker 26, and the display unit 27 displays the real-time image which changes as the shock wave applicator 17 is moved. When the renal calculus 39 is found on the display unit 27, the shock wave applicator 17 is adjusted carefully to place the focal point marker 26 on the image of the renal calculus 39. When the focal point marker 26 is placed on the image of the renal calculus 39, the shock wave applicator 17 is fixed at that position.

Next, the operator operates the pulse generation switch 29 to provide the control signal to the pulser 18 through the CPU 22 and the timing controller 23. In response, the pulser 18 provides the pulse signals to the shock wave transducer 15 and the shock wave transducer 15 transmits the ultrasonic shock waves focused toward the renal calculus 39 located at the position of the focal point marker 26 which subsequently destroy the renal calculus 39 by their concentrated energy.

The similar procedure is repeated until the entire renal calculus 39 is completely destroyed.

In a case of an ultrasonic thermal treatment apparatus, the apparatus has a configuration similar to the shock wave medical treatment apparatus described above, except that the pulser 18 provides continuous oscillation signals such that the shock wave transducer 15 transmits continuous ultrasonic waves instead of the ultrasonic shock waves, which destroy the treatment target by using a thermal effect of the continuous ultrasonic waves.

Now, in such a conventional ultrasonic wave medical treatment apparatus, it is generally considered preferable to carry out the treatment process while checking the effect of the treatment several times in a course of its progress because it is rather usual for the treatment target as well as the patient to be moving around during the treatment process due to the breathing by the patient or other causes.

However, in a conventional ultrasonic wave medical treatment apparatus, the treatment process is set out completely at the beginning and carried out altogether at once as set out in advance, so that it has been difficult to check the effect of the treatment in the course of progress in the treatment. This implies that efficient treatment may not be carried out depending on the setting at the beginning. On the other hand, when the entire treatment process is divided into several sections and each section is carried out separately, it is necessary in a conventional ultrasonic medical treatment apparatus to make a setting at a beginning of each section, so that the treatment process can be executed efficiently.

SUMMARY OF THE INVENTION

It is therefore an object of the present invention to provide a method and apparatus for ultrasonic wave medical treatment in which it is possible to cheek the effect of the treatment in a course of a progress of the treatment process, while executing the treatment process efficiently.

According to one aspect of the present invention there is provided an ultrasonic wave medical treatment apparatus, comprising: setting means for setting a total number of ultrasonic wave irradiations for an entire ultrasonic wave medical treatment process which is divided into a plurality of sections, and a sectional number of ultrasonic wave irradiations for each of the plurality of sections; ultrasonic wave irradiation means for irradiating ultrasonic waves on a treatment target for the total number of ultrasonic wave irradiations; control means for controlling the ultrasonic wave irradiation means such that the ultrasonic waves are irradiated as many times as the sectional number of ultrasonic wave irradiations for each of the plurality of sections and then the ultrasonic wave irradiation is paused before the ultrasonic wave irradiation for a subsequent one of the plurality of sections is executed; and means for notifying that the ultrasonic wave irradiation for each of the plurality of sections is completed by generating a notification sound when the ultrasonic waves are irradiated as many times as the sectional number of ultrasonic wave irradiations successively.

According to another aspect of the present invention there is provided a method of ultrasonic wave medical treatment, comprising the steps of: dividing an entire ultrasonic wave medical treatment process into a plurality of sections; setting a total number of ultrasonic wave irradiations for the entire ultrasonic wave medical treatment process and a sectional number of ultrasonic wave irradiations for each of the plurality of sections; irradiating ultrasonic waves on a treatment target as many times as the of ultrasonic wave irradiations for each of the plurality of sections and the ultrasonic wave irradiation is paused before the ultrasonic wave irradiation for a subsequent one of the plurality of sections is executed; and notifying that the ultrasonic wave irradiation for each of the plurality of sections is completed by generating a notification sound when the ultrasonic waves are irradiated as many times as the sectional number of ultrasonic wave irradiations successively.

According to another aspect of the present invention there is provided an ultrasonic wave medical treatment apparatus, comprising: setting means for setting a total number of ultrasonic wave irradiations for an entire ultrasonic wave medical treatment process which is divided into a plurality of sections, and a sectional number of ultrasonic wave irradiations for each of the plurality of sections; ultrasonic wave irradiation means for irradiating ultrasonic waves on a treatment target as many times as the total number of ultrasonic wave irradiations; control means for controlling the ultrasonic wave irradiation means such that the ultrasonic waves are irradiated as many times as the sectional number of ultrasonic wave irradiations for each of the plurality of sections and then the ultrasonic wave irradiation is paused before the ultrasonic wave irradiation for a subsequent one of the plurality of sections is executed; imaging means for obtaining tomographic images of the treatment target; and image memory means for recording the tomographic images obtained by the imaging means in a course of the entire ultrasonic wave medical treatment process.

According to another aspect of the present invention there is provided a method of ultrasonic wave medical treatment, comprising the steps of: dividing an entire ultrasonic wave medical treatment process into a plurality of sections; setting a total number of ultrasonic wave irradiations for the entire ultrasonic wave medical treatment process and a sectional number of ultrasonic wave irradiations for each of the plurality of sections; irradiating ultrasonic waves on a treatment target as many times as the total number of ultrasonic wave irradiations, such that the ultrasonic waves are irradiated as many times as the sectional number of ultrasonic wave irradiations for each of the plurality of sections and then the ultrasonic wave irradiation is paused before the ultrasonic wave irradiation for a subsequent one of the plurality of sections is executed; obtaining tomographic images of the treatment target; and recording the tomographic images obtained in a course of the entire ultrasonic wave medical treatment process.

Other features and advantages of the present invention will become apparent from the following description taken in conjunction with the accompanying drawings.

DETAILED DESCRIPTION OF THE PREFERRED EMBODIMENTS

Figure 1:
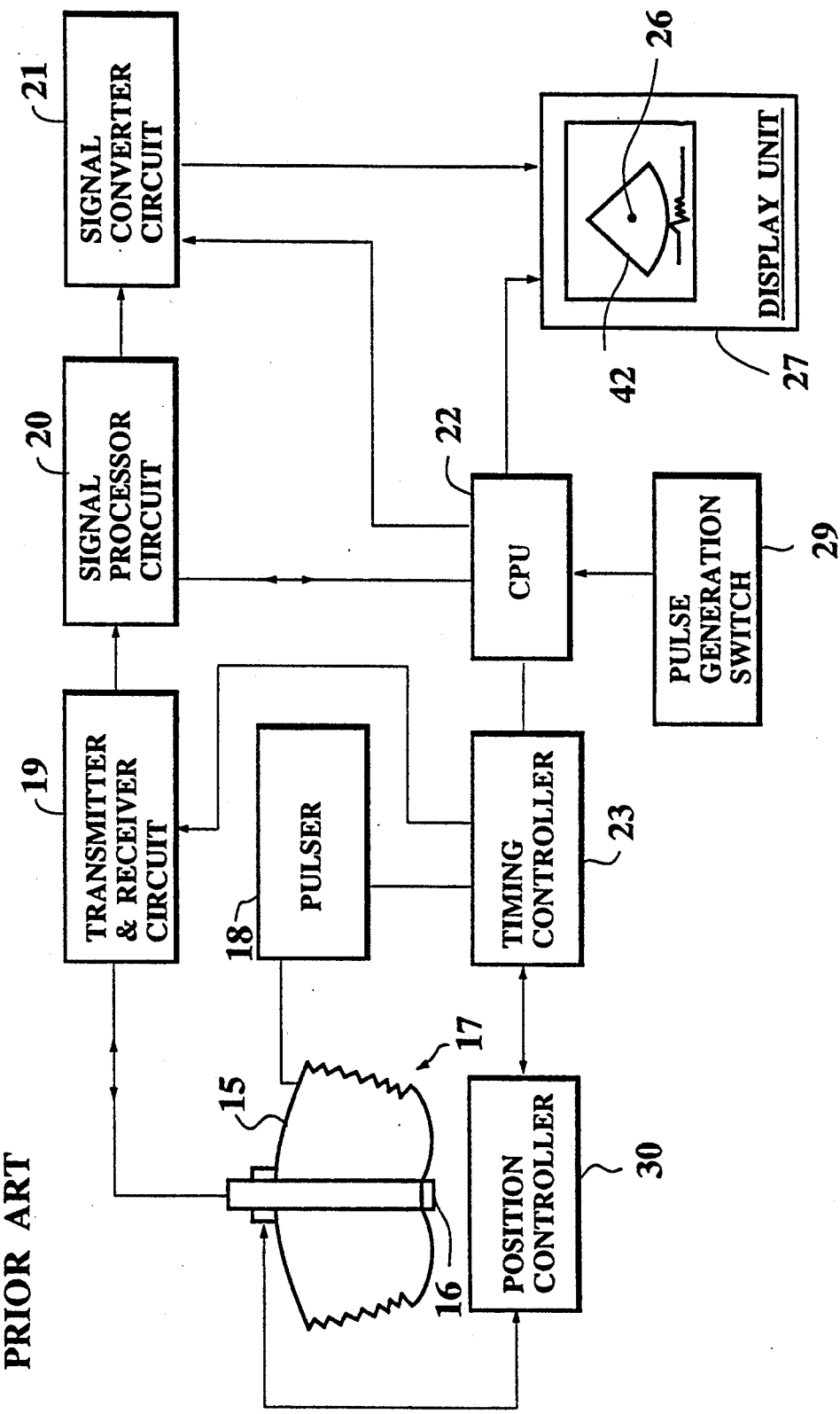
FIG. 1 is a block diagram of an example of a conventional shock wave medical treatment apparatus.
Figure 2:
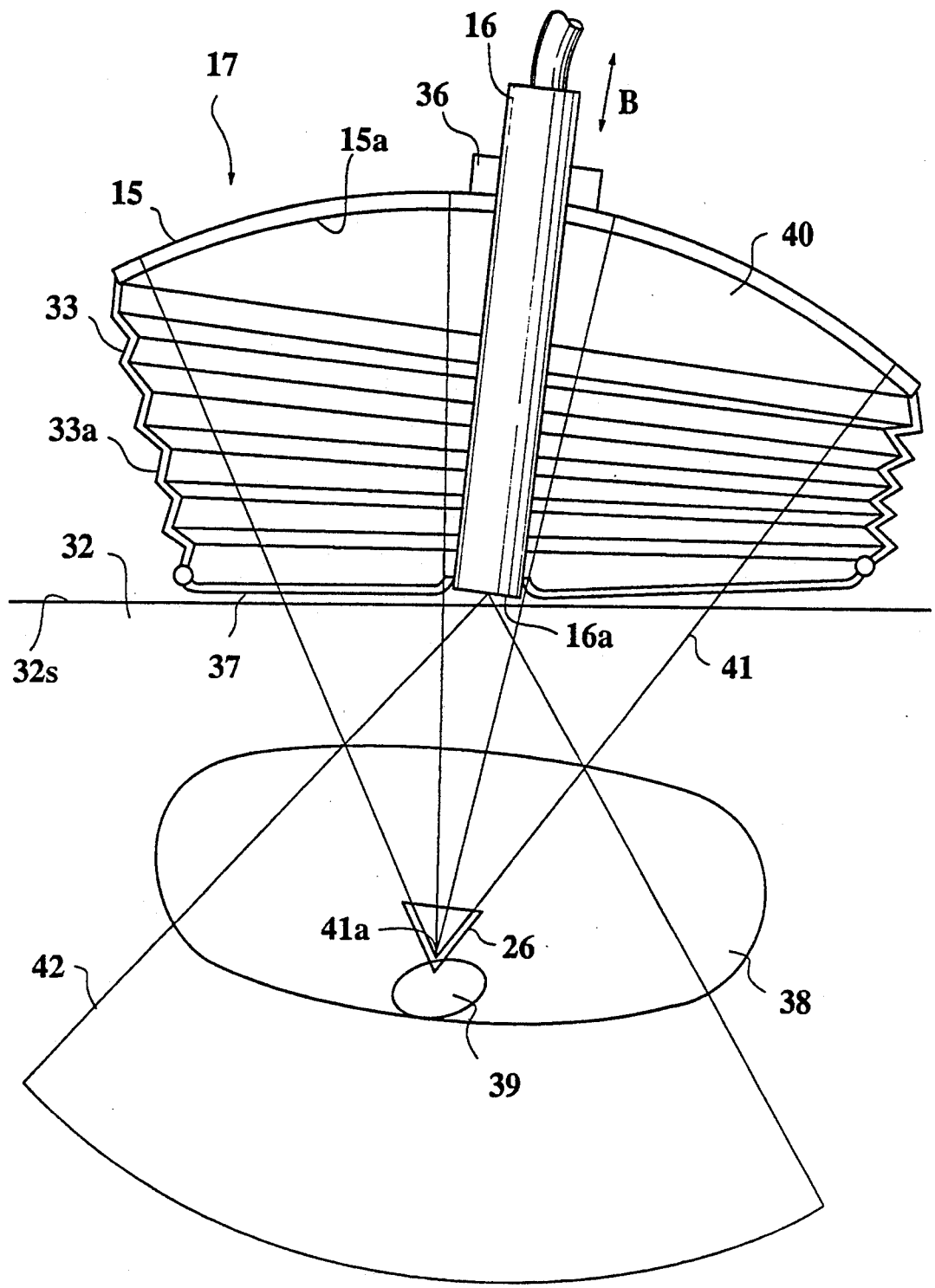
FIG. 2 is a detailed diagram of a shock wave applicator in the shock wave medical treatment apparatus of FIG. 1.
Figure 3:
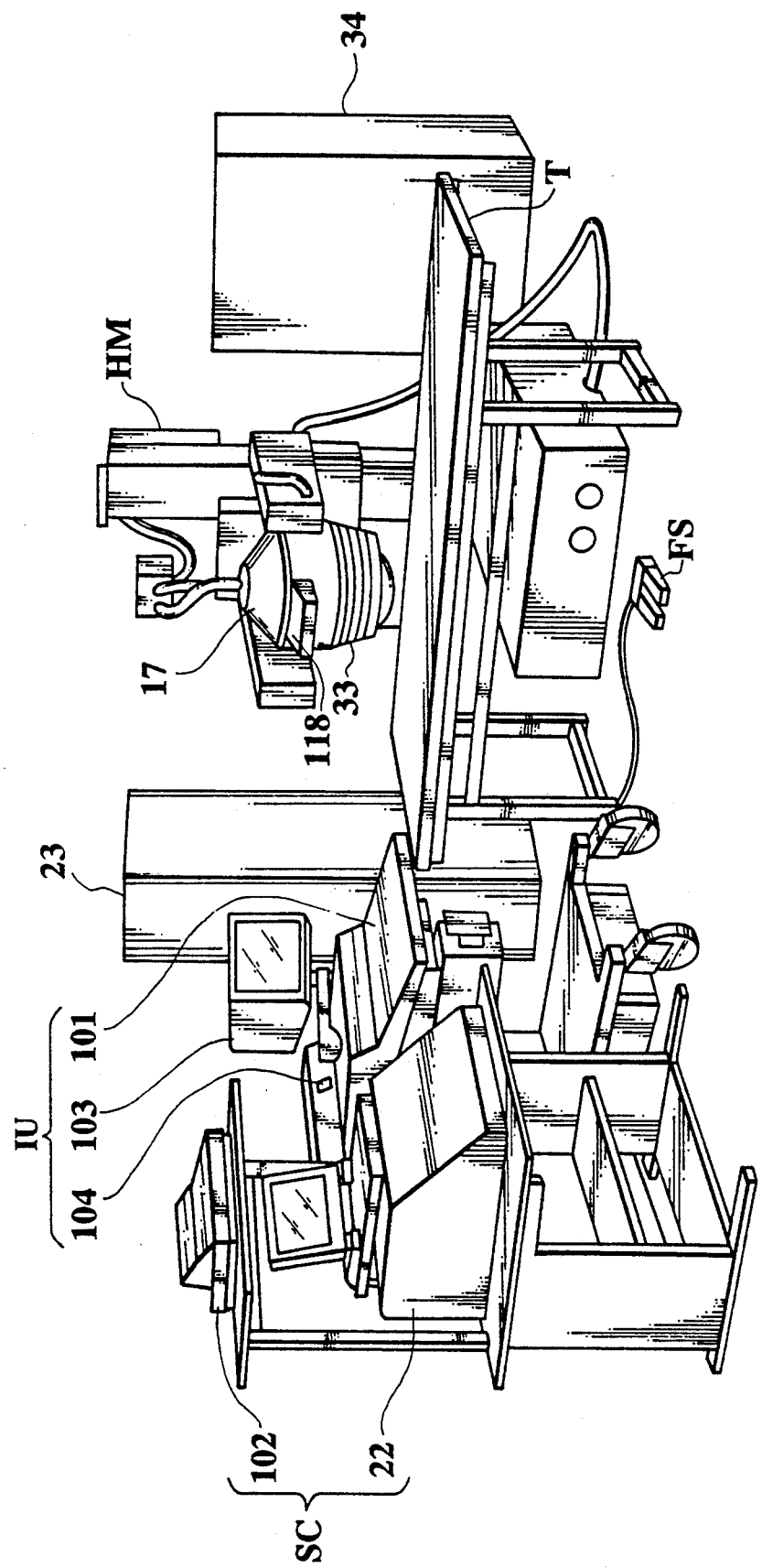
FIG. 3 is a perspective illustration of one embodiment of an ultrasonic wave medical treatment apparatus according to the present invention.

Referring now to FIG. 3, one embodiment of an ultrasonic wave medical treatment apparatus according to the present invention in a form of a shock wave medical treatment apparatus will be described. In the following description, those elements which are substantially equivalent to the corresponding elements in a conventional shock wave medical treatment apparatus of FIGS. 1 and 2 described above will be given the same labels and reference numerals in the drawings.

In this embodiment, the shock wave medical treatment apparatus generally comprises: a shock wave applicator 17 for applying the ultrasonic shock waves to a patient on a bed T; an applicator supporting unit HM for supporting and moving the shock wave applicator 17 over the patient; a foot step with which the operator controls the applicator supporting unit HM by foot; a supporting unit control panel 118 attached to the shock wave applicator 17 at which the operator enters commands for controlling the applicator supporting unit HM; a water controller 34 for controlling an amount of water in a water bag 33 of the shock wave applicator 17; an imaging unit IU including a shock wave irradiation condition setting unit 101 for entering a setting of the ultrasonic shock waves to be transmitted from the shock wave applicator 17, a timing controller 23 for controlling process timings for the shock wave treatment; a display unit 103 for displaying information on the shock wave treatment to the operator in addition to a fan shaped acoustic region 42 and a focal point marker 26; a notice sound generation unit 104 for generating a notice sound to the operator; a system controller SC including a irradiated shock wave data output unit 102 for outputting data on the ultrasonic shock waves actually transmitted from the shock wave applicator 17, and a CPU 22 for controlling the operation of each element of the apparatus.

Figure 4:
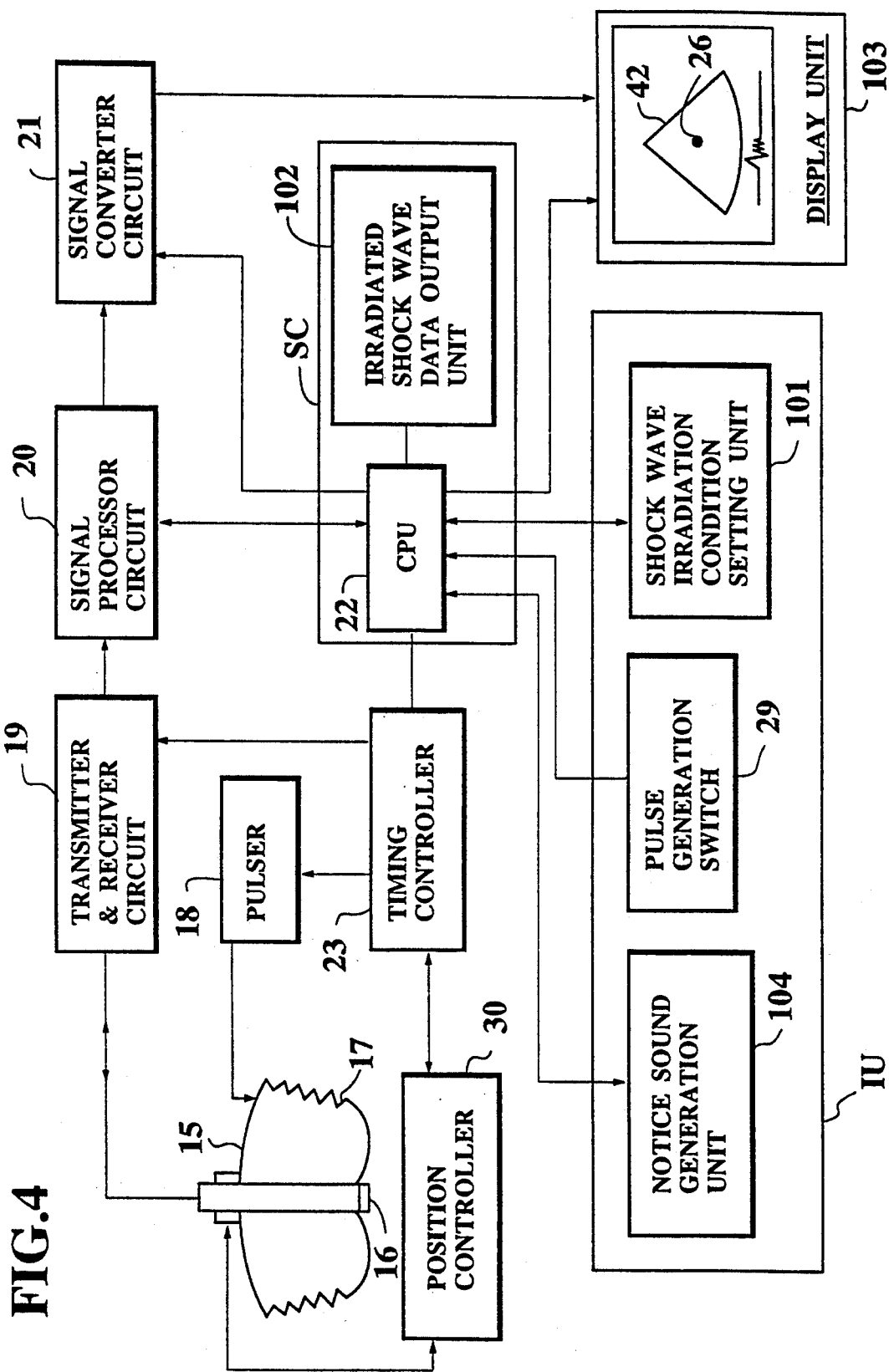
FIG. 4 is a block diagram of the ultrasonic wave medical treatment apparatus of FIG. 3.

In addition, as shown in FIG. 4, the shock wave applicator 17 includes a shock wave transducer 15 for transmitting ultrasonic shock waves, and an ultrasonic wave transducer 16 for transmitting imaging ultrasonic waves to carry out a B mode scanning (tomographic imaging) and receiving echo signals resulting from the B mode scanning. This shock wave applicator 17 has further details similar to those shown in FIG. 2.

Moreover, as shown in FIG. 4, this shock wave medical treatment apparatus further comprises: a pulser 18 for providing pulse signals to drive the shock wave transducer 15; a transmitter and receiver circuit 19 for providing pulse signals to drive the ultrasonic wave transducer 16, and collecting the echo signals received by the ultrasonic wave transducer 16; a signal processor circuit 20 for converting the echo signals collected by the transmitter and receiver circuit 19 into video signals by applying amplitude detection; a signal converter circuit 21 such as a digital scan converter for performing signal conversion on the video signals obtained by the signal processor circuit 20; a pulse generation switch 29 connected to the CPU 22 for setting the timings for generating the pulse signals to be given from the pulser 18 to the shock wave transducer 15; and a position controller 30 for adjusting the relative position of the shock wave transducer 15 and the ultrasonic wave transducer 16.

The shock wave irradiation condition setting unit 101 is a unit by which the operator sets up the shock wave irradiation condition, including the total number of shock wave irradiations (total shot number), the rate of the shock wave irradiation (pulse rate), driving voltage for the shock waves, and the number of shock wave irradiations between pauses (pause shot number). The total shot number is a total number of shock wave irradiations in the entire shock wave treatment. The pulse rate is a number of shock wave irradiation per unit time, where a pulse rate of 2.0 Hz indicates two shots per second for example. The driving voltage is a voltage applied by the pulse signals to the shock wave transducer 15, which determines the strength of the shock waves to be irradiated. The pause shot number is a number of shock wave irradiations within each section of the shock wave treatment where the entire shock wave treatment is divided into a number of sections by pauses (temporarily stopping of the shock wave irradiation), and where the pause shot number of 300 indicates that the irradiation of shock waves temporarily stops after 300 shots for example.

In setting the shock wave irradiation condition at this shock wave irradiation condition setting unit 101, the operator first sets up the total shot number by manipulating up and down buttons 201 and 202 located by a total shot number indicator 206, where the total shot number increases or decreases by a single pressing of the up button 201 or down button 202, respectively. This setting of the total shot number such as 3000 shown in the total shot indicator 206 of FIG. 5 will not change until the cancellation of the setting is enacted by a pressing of a clear button 203 located by a current shot number indicator 207 for indicating a number of shock waves actually irradiated during the shock wave treatment which increases one by one as the shock waves are actually Irradiated. The individual irradiation of the shock wave is also indicated by a flashing of a shooting lamp 209 located by the current shot number indicator 207 during the actual shock wave treatment.

Similarly, the operator next sets up the pause shot number by manipulating up and down buttons 204 and 205 located by a pause/remaining shot number indicator 208, where the pause shot number also increases or decreases by a single pressing of the up button 204 or down button 205, respectively. This setting of the pause shot number such as 300 shown in the pause/remaining shot indicator 208 of FIG. 5 will not change until the cancellation of the setting is enacted by a pressing of the clear button 203. During the actual shock wave treatment, the indication of the pause/remaining shot number indicator 208 decreases one by one as the shock waves are actually irradiated, and returns immediately to the pause shot number setting whenever the shock wave treatment reaches a pause.

Next, the operator sets up the driving voltage by manipulating a knob 213 located below a driving voltage indicator 211, where the driving voltage increases or decreases in units of 1 KV.

Similarly, the operator next sets up the pulse rate by manipulating a knob 214 located below a pulse rate indicator 212, where the pulse rate increases or decreases in units of 0.5 Hz.

In addition, the front setting panel of the shock wave irradiation condition setting unit 101 also has a pulser ready lamp 210 which lights on when the pulser 18 is ready to operate at the settings indicated by the driving voltage indicator 211 and the pulse rate indicator 212.

Figure 6:
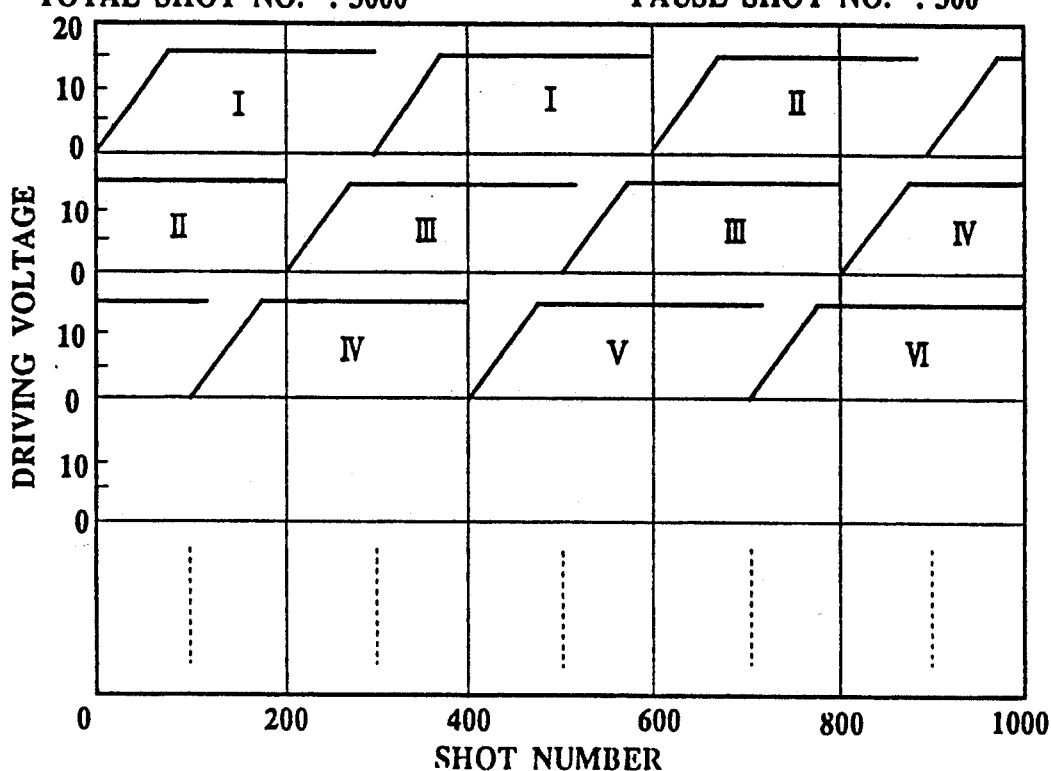
FIG. 6 is an illustration of irradiated shock wave data to be outputted by an irradiated shock wave data output unit in the ultrasonic wave medical treatment apparatus of FIG. 3.

The irradiated shock wave data output unit 102 can be any output device such as a printer used in a ordinary personal computer which outputs the irradiated shock wave data in a form shown in FIG. 6 which comprises: a patient treatment record such as a patient ID and treatment date and time; shock wave irradiation condition settings for the total shot number, pause shot number, driving voltage, and pulse rate which are set at the shock wave irradiation condition setting unit 101; and a graphic chart of the driving voltage as a function of the shot number, where the chart in which the driving voltage is graphed along a vertical axis having 20 KV scale and the shot number is graphed along a horizontal axis having 1000 shots is depicted in several lines. The scales on the vertical and horizontal axes may change according to the settings of the total shot number and the driving voltage. The patient ID may include a patient name, a location of a calculus, a size of a calculus, and other relevant information in coded forms.

Figure 5:
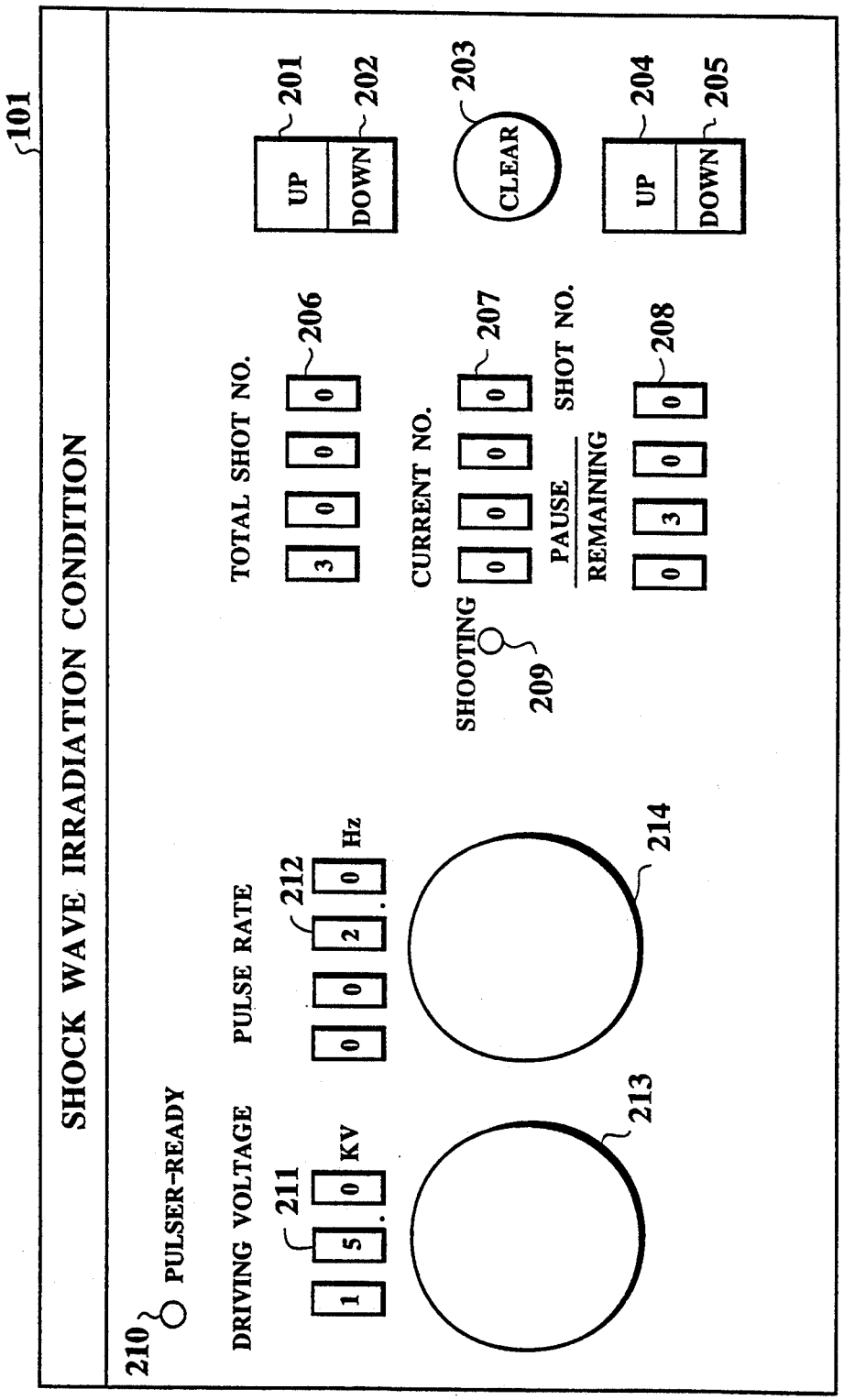
FIG. 5 is an Illustration of a front panel of a shock wave irradiation condition setting unit in the ultrasonic wave medical treatment apparatus of FIG. 3.
Figure 7:
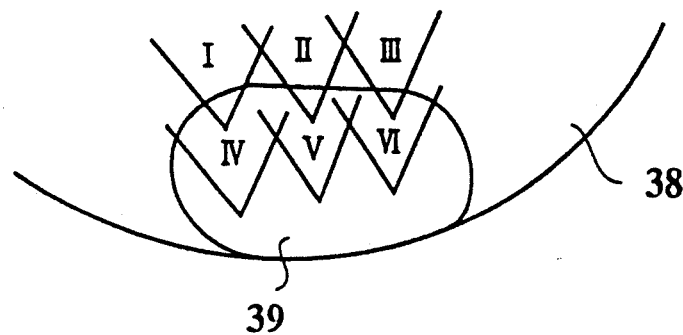
FIG. 7 is an illustration of a renal calculus to be treated by the ultrasonic wave medical treatment apparatus of FIG. 3 indicating various positions for a focal point of the shock waves.

In this embodiment, according to the shock wave irradiation condition settings shown in FIG. 5, the shock wave irradiation pauses after every 300 shots as shown in FIG. 6. At each pause, the focal point of the shock waves are sequentially shifted as shown in FIG. 7, from a position I for the first 300 shots, to a position II for next 300 shots, a position III for next 600 shots, a position IV for next 300 shots, a position V for next 300 shots, and finally a position VI for next 300 shots. Moreover, after each pause, the driving voltage is gradually increased from 0 V to the setting value of 15 KV, so as to secure the safety in the continuation of the shock wave treatment after the pause during which the shock wave focal point had been shifted. For example, the driving voltage is increased in steps of 1 KV per every 4 pulses for a case in which the total shot number is up to 4000 shots, in steps of 1 KV per every 8 pulses for a case in which the total shot number lies between 4001 to 8000 shots, and in steps of 1 KV per every 10 pulses for a case in which the total shot number is greater than 8000. Such an increment rate of the driving voltage may be set as a part of the shock wave irradiation condition.

Figure 8:
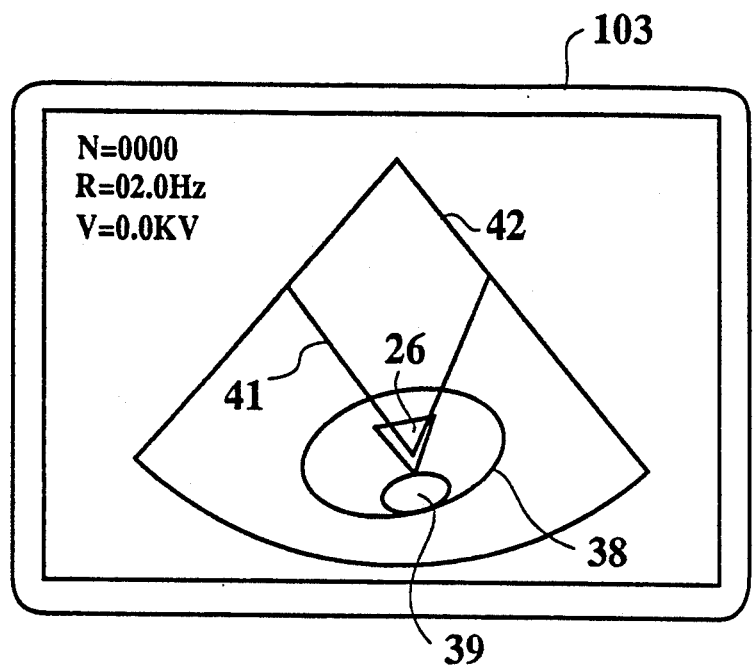
FIG. 8(A) is an illustration of a display on a display unit in the ultrasonic wave medical treatment apparatus of FIG. 3 at one stage in a course of the shock wave treatment process.
FIG. 8(B) is an illustration of a display on a display unit in the ultrasonic wave medical treatment apparatus of FIG. 3 at another stage in a course of the shock wave treatment process.
Figure 8:
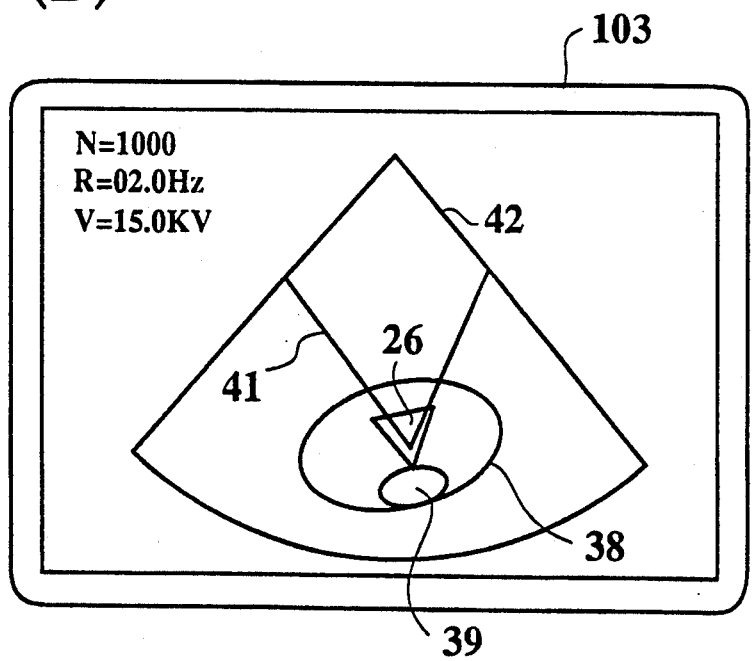

As shown in FIGS. 8(A) and 8(B), the display unit 103 displays the image of the kidney 38 and the renal calculus 39 in relation to the fan shaped acoustic region 42, the shock wave region 41, and the focal point marker 26, along with the current values for the shot number N, the pulse rate R, and the driving voltage V.

The notice sound generation unit 104 is equipped with a sound memory and a speaker, and generates a notice sound for notifying the operator that the shock wave treatment has reached the pause and the shock wave irradiation has stopped whenever the shock wave treatment reaches the pause and the shock wave irradiation stops by the prerecorded notice sound memorized in the sound memory. This generation of the notice sound from the notice sound generation unit 104 is activated in response to a pausing signal outputted by the shock wave irradiation condition setting unit 101 through the CPU 22 whenever the shock wave treatment reaches a pause. The notice sound may be in the form of a vocal message or an alarm sound.

The operation of this shock wave medical treatment apparatus will be described along the actual shock wave treatment process.

First, the operator controls the supporting unit control panel 118 such that the shock wave applicator 17 is positioned over the patient 32 such that the bottom side 37 of the water bag 33 makes a contact with a surface 32S of the patient over the kidney 39.

Then, by using the ultrasonic wave transducer 16, the tomographic image of the patient 32 is obtained and displayed on the display unit 103 along with the acoustic field 42, shock wave region 41, and focal point marker 26. Here, the transmitting and receiving surface 16a of the ultrasonic wave transducer 16 also makes a contact with the surface 32S, so that a clear tomographic image unaffected by the bottom side 37 of the water bag 33 or the water can be obtained.

Next, when the image of the kidney 38 is obtained on the display unit 103, the renal calculus 39 is searched for on the display unit 103. Here, the display unit 103 displays the real-time image, which changes as the shock wave applicator 17 is moved according to commands from the operator.

When the renal calculus 39 is found on the display unit 103, the operator determines the shock wave irradiation condition settings according to the position and size of the renal calculus 39, and enters these settings at the shock wave irradiation condition setting unit 101. When the setting of the shock wave irradiation condition is completed, the current values for the shot number N, the pulse rate R, and the driving voltage V are also displayed on the display unit 103 as described above. Thus, immediately after the completion of the shock wave irradiation condition, the display on the display unit 103 appears as shown in FIG. 8(A), while after 1000 shots, the display of the display unit 103 appears as shown in FIG. 8(B).

Next, the operator operates the pulse generation switch 29 to provide the control signal to the pulser 18 through the CPU 22 and the timing controller 23. In response, the pulser 18 provides the pulse signals to the shock wave transducer 15 and the shock wave transducer 15 transmits the ultrasonic shock waves focused toward the renal calculus 39 located at the position of the focal point marker 26 which subsequently destroy the renal calculus 39 by their concentrated energy.

The similar procedure is repeated until the entire renal calculus 39 is completely destroyed.

After the completion of the entire shock wave treatment, the irradiated shock wave data shown in FIG. 6 is outputted from the irradiated shock wave data output unit 102.

Figure 9:
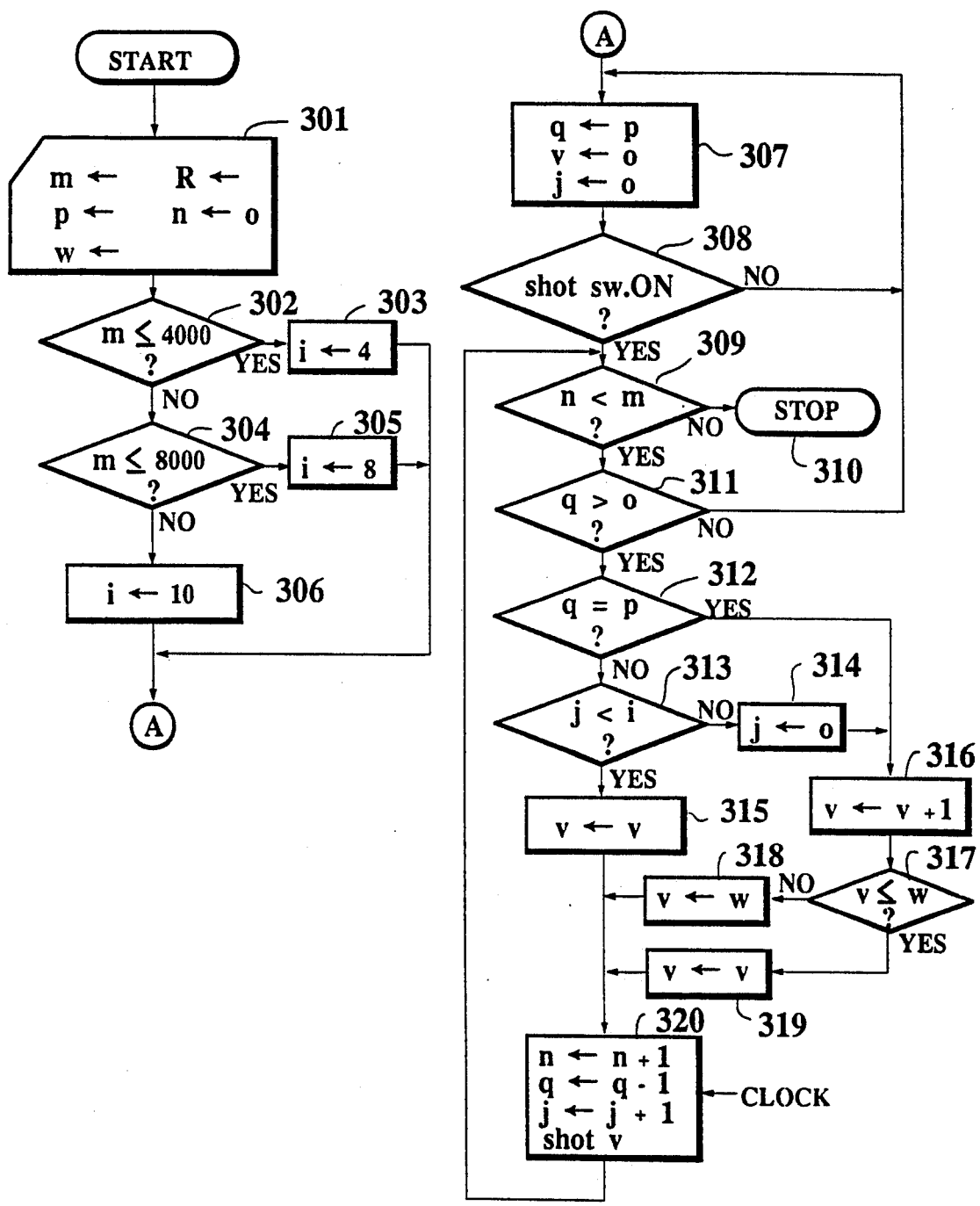
FIG. 9 is a flow chart for a control operation by a CPU in the ultrasonic wave medical treatment apparatus of FIG. 3.

Referring now to the flow chart of FIG. 9, the control by the CPU 22 in the above described shock wave treatment process will be described.

First at the step 301, the settings for the total shot number m, driving voltage w, pulse rate R, and pause shot number p are given from the shock wave irradiation condition setting unit 101, while the shot number n is set to an initial value of 0. The pulse rate will be controlled by using a clock signal of the CPU 22 throughout the subsequent operation.

Then, at the steps 302 to 306, the increment rate i for the driving voltage is set up. Namely, as already described above, the increment rate is set such that the driving voltage is increased in steps of 1 KV per every 4 pulses for a case in which the total shot number is up to 4000 shots by the steps 302 and 303, in steps of 1 KV per every 8 pulses for a case in which the total shot number lies between 4001 to 8000 shots in the steps 304 and 305, and in steps of 1 KV per every 10 pulses for a case in which the total shot number is greater than 8000 by the step 306. The increment rate may be set in steps of 0.5 KV or 10 KV per unit time instead.

Next, at the step 307, a current remaining shot number q is set equal to the pause shot number p, while current driving voltage v and a current increment rate j are set to 0, and the input of the control signal from the pulse generation switch 29 is awaited.

When the control signal is entered at the step 308, if the shot number n becomes equal to the total shot number m at the step 309 the shock wave treatment finishes at the step 310. If the current remaining shot number q becomes equal to 0 at the step 311, the process returns to the step 307, and the CPU 22 controls the notice sound generation unit 104 in order to notify the operator about the pause.

Otherwise, next at the steps 312 to 319, the driving voltage is increased from 0 to the setting value w, and the shooting command is given to the timing controller 23, in response to which the pulser 18 is activated to make the shock wave irradiated from the shock wave applicator 17, while the shot number n, current remaining shot number q, and the current increment rate j are updated, and then the process returns to the step 309.

Thus, according to this embodiment, the shock wave irradiation is carried out in a number of sections separated by the pauses, so that the excessive irradiation or the unnecessary irradiation of the shock wave can be avoided because it is possible for the operator to cheek the effect of the treatment in a course of a progress of the treatment process during the pauses.

In addition, the notice sound is generated from the notice sound generation unit 104 whenever the shock wave treatment reaches the pause, so that the operator can proceed promptly to the operation to be carried out during the pause, while the patient can relax from the constrained posture required during the shock wave irradiation. Thus, the treatment process can be executed very efficiently.

Moreover, according to this embodiment, the driving voltage is increased gradually from 0 to the setting value, so that the shock wave irradiation can be carried out very safely, without a danger of causing a pain to the patient by the sudden shock wave irradiation.

It is to be noted that the shock wave medical treatment apparatus of the above embodiment can be changed into an ultrasonic thermal treatment apparatus by replacing the pulser 18 by a continuous oscillation pulser for providing continuous oscillation signals such that the shock wave transducer 15 transmits the continuous ultrasonic waves instead of the ultrasonic shock waves, which destroy the treatment target by using the thermal effect of the continuous ultrasonic waves.

It is also noted that the notice sound generation unit 104 in the above embodiment may be replaced by another notification device, such as a visual message generation device.

It is also to be noted that the updating timing for the current state of the shock wave irradiation displayed on the display unit 103 is sufficient to have less than a few msec delay from the actual shock wave irradiation.

Furthermore, it is also to be noted that in the course of shock wave treatment, described above, other medically useful records may be outputted from an output device, monitored on a display device, or recorded in a recording device.

In particular, it is extremely useful to record the images on the display unit 103 at various stages in a course of the shock wave treatment process, which can be valuable references for the subsequent shock wave treatments of the other patients.

Figure 10:
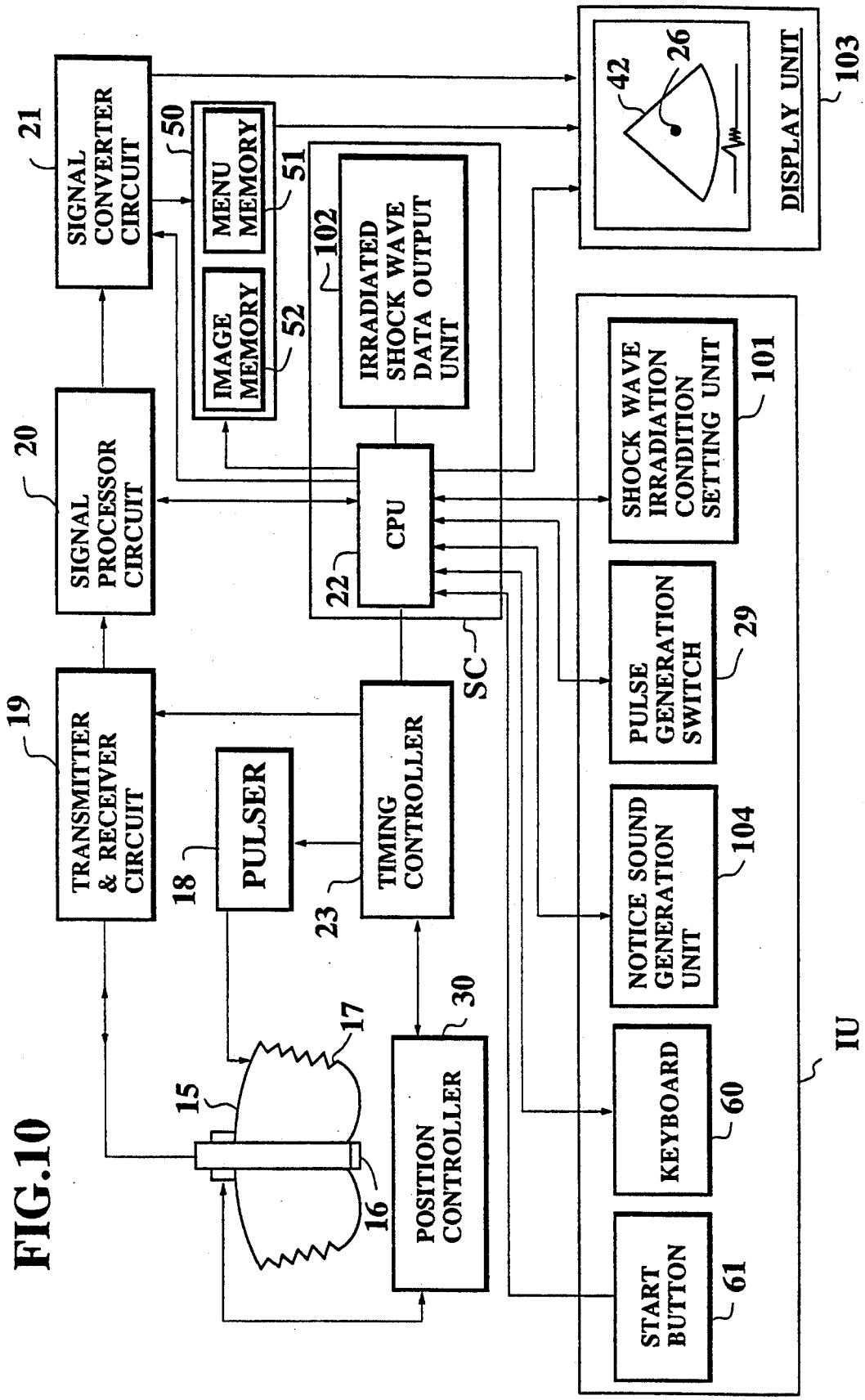
FIG. 10 is a block diagram of another embodiment of an ultrasonic wave medical treatment apparatus according to the present invention.

Referring now to FIG. 10, another embodiment of the shock wave medical treatment apparatus, which can be regarded as a variation of the above described embodiment, will be described. In the following description, those elements which are substantially equivalent to the corresponding elements in the shock wave medical treatment apparatus of FIGS. 3 and 4 described above will be given the same labels and reference numerals in the drawings, and their descriptions will be omitted.

In this embodiment, the apparatus is modified such that the images on the display unit 103 at various stages in a course of the shock wave treatment process can be recorded automatically, and the shock wave treatment process can be carried out automatically, according to a treatment plan set up by the operator in advance.

Namely, as shown in FIG. 10, the shock wave medical treatment apparatus of this embodiment has additional elements of a memory unit 50 comprising a menu memory 51 for memorizing a treatment plan menu, and an image memory 52 for memorizing the images to be displayed on the display unit 103 at various stages in a course of the shock wave treatment process by receiving image data from the signal converter circuit 21; a keyboard 60 for changing the treatment plan menu in the menu memory 51; and a start button 61 for initiating an automatic execution of the shock wave treatment process according to the treatment plan menu in the menu memory 51.

Figure 11:
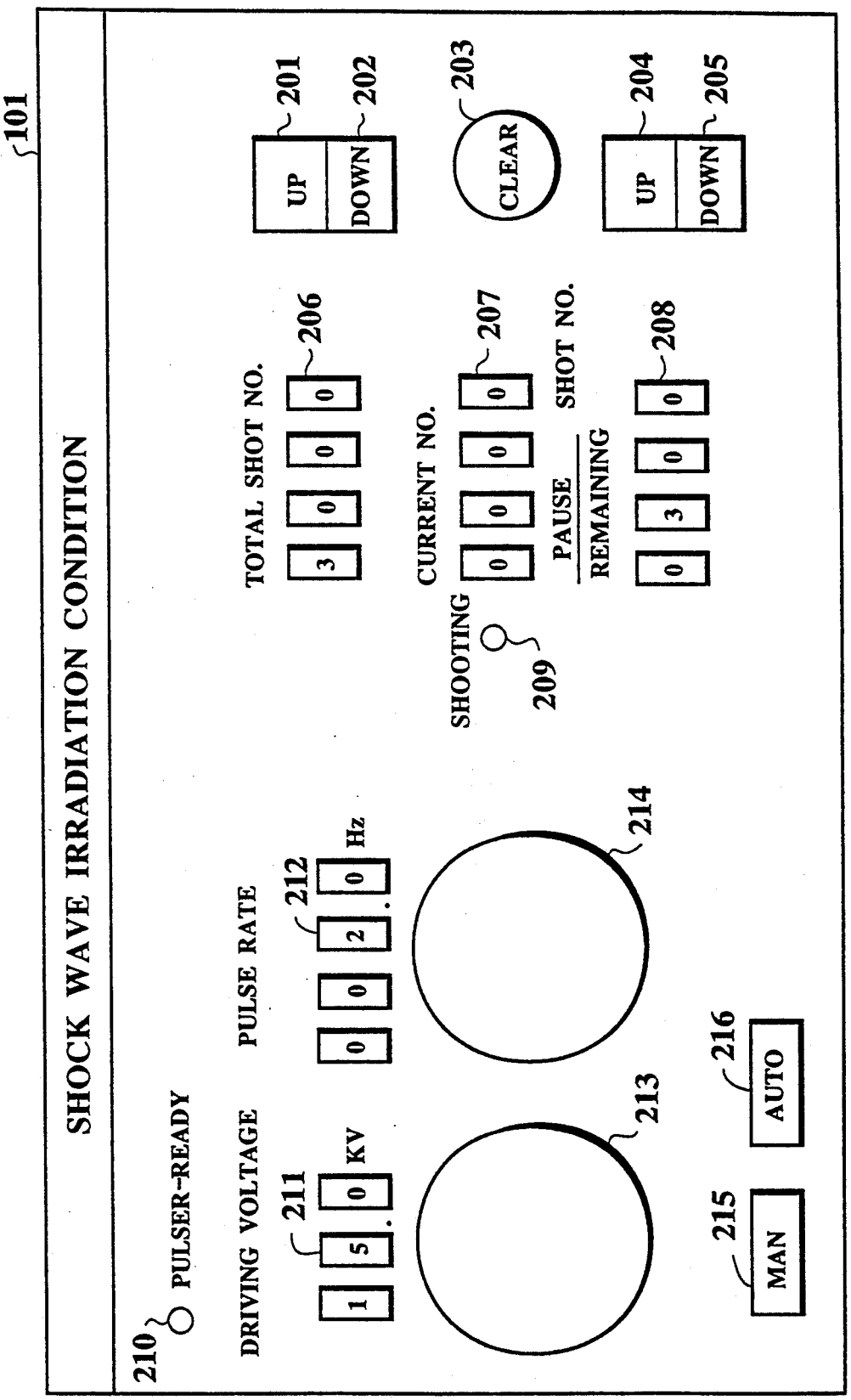
FIG. 11 is an illustration of a front panel of a shock wave irradiation condition setting unit in the ultrasonic wave medical treatment apparatus of FIG. 10.

Furthermore, as shown in FIG. 11, the shock wave irradiation condition setting unit 101 has the additional elements of a manual button 215 and an automatic button 216. The manual button 215 is pressed down by the operator when the operator wishes to set up the shock wave irradiation condition manually at the shock wave irradiation condition setting unit 101, as described in the above embodiment. On the other hand, the automatic button 216 is pressed down by the operator when the operator wishes to use the automatic execution of the shock wave treatment process according to the treatment plan menu.

Figure 12:
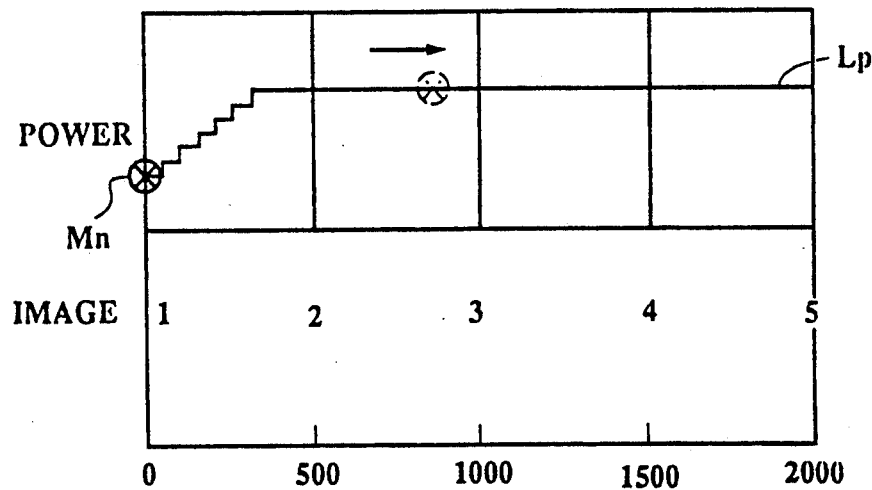
FIG. 12 is an illustration of a treatment plan menu wave data to be utilized in the ultrasonic wave medical treatment apparatus of FIG. 10.

When the automatic button 216 is pressed down, a treatment plan menu shown in FIG. 12 is displayed on the display unit 103, where each entry in the treatment plan menu can be changed by operating the keyboard 60.

The treatment plan menu of FIG. 12 contains an image recording plan and a shock wave irradiation plan along with their graphic representation.

The image recording plan has entries for a shot number of a first image recording (start shot number), a shot number of a last image recording (stop shot number), and a shot number interval between two image recordings (step shot number), which are set to be 0, 2000, and 500, respectively in FIG. 12. Thus, according to this image recording plan, the image on the display unit 103 is recorded first before the first shock wave irradiation, and thereafter every 500 shots, until the 2000-th shot. It is noted that image recording by the image memory 52 can also be activated quite independently from the image recording plan, by the designated commanding operation on the keyboard 60 by the operator at any time during the shock wave treatment process.

The shock wave radiation plan has entries for a starting irradiation power (start power), a target irradiation power (stop power), a power increment interval (step power), a number of shots per unit power increment (power step shot number), and the pause shot number, which are set to be 20%, 90%, 10%, 50, and 200, respectively, in FIG. 12. Thus, according to this shock wave irradiation plan, the shock wave irradiation starts out at 20% of a maximum irradiation power and increases by 10% per 50 shots until the irradiation power reaches 90% of the maximum irradiation power, while stopping at every 200 shots.

These image recording plan and the shock wave irradiation plan are also shown in the graphic representation in which the irradiation power is graphed along the vertical axis and the shot number is graphed along the horizontal axis along with indications for the image recording timings and a current state marker Mn, which traces the irradiation power line Lp as the shock wave treatment process proceeds.

In this embodiment, after positioning of the shock wave applicator 17 is completed, the operator presses the manual button 215 or the automatic button 216. When the manual button 215 is pressed, the subsequent shock wave treatment process proceeds as in the previous embodiment. On the other hand, when the automatic button 216 is pressed, the treatment plan menu of FIG. 12 is displayed on the display unit 103 on which the operator makes changes if necessary by using the keyboard 60, and then the operator presses the start button 61. In response to this pressing of the start button 61, the CPU 22 automatically controls the timing controller 23 and the image memory 52 according to the shock wave irradiation plan and the image recording plan set in the treatment plan menu, such that the shock wave irradiation and the image recording can be executed automatically.

Thus, according to this embodiment, in addition to the advantages enumerated above for the previous embodiment, the shock wave irradiation and the image recording can be carried out automatically during the shock wave treatment process according to the treatment plan menu prepared by the operator in advance, so that the task of the operator can be reduced during the shock wave treatment operation.

Moreover, because of the current state marker Mn provided on the graphic representation of the shock wave irradiation plan and the image recording plan in the treatment plan menu, the operator can comprehend the progress of the shock wave treatment process easily by monitoring of the treatment plan menu.

It is to be noted that various modifications such as those already described above for the previous embodiment are also possible for this embodiment.

It is also to be noted that the method and apparatus of the present invention as described above are equally applicable to a shock wave medical treatment apparatus other than the ultrasonic shock wave medical treatment apparatus described above as the preferred embodiments, such as the so called spark gap type shock wave medical treatment apparatus which uses the shock waves generated electrically instead of the ultrasonic transducer.

Besides these, many modifications and variations of the above embodiments may be made without departing from the novel and advantageous features of the present invention. Accordingly, all such modifications and variations are intended to be included within the scope of the appended claims.

What is claimed is:

1. An ultrasonic wave medical treatment apparatus, comprising:

setting means for setting a total number of ultrasonic wave irradiations for an entire ultrasonic wave medical treatment process which is divided into a plurality of sections, and a sectional number of ultrasonic wave irradiations for each of the plurality of sections;

ultrasonic wave irradiation means for irradiating ultrasonic waves on a treatment target as many times as the total number of ultrasonic wave irradiations;

control means for controlling the ultrasonic wave irradiation means such that the ultrasonic waves are irradiated as many times as the sectional number of ultrasonic wave irradiations for each of the plurality of sections and then the ultrasonic wave irradiation is paused before the ultrasonic wave irradiation for a subsequent one of the plurality of sections is executed; and means for notifying that the ultrasonic wave irradiation for each of the plurality of sections is completed by generating a notification sound when the ultrasonic waves are irradiated as many times as the sectional number of ultrasonic wave irradiations successively.

2. The apparatus of claim 1, wherein the ultrasonic wave irradiation means irradiates the ultrasonic waves in the form of shock waves.

3. The apparatus of claim 1, wherein the ultrasonic wave irradiation means irradiates the ultrasonic waves in the form of continuous ultrasonic waves.

4. The apparatus of claim 1, wherein the control means also controls the ultrasonic wave irradiation means such that in the ultrasonic wave irradiation for each of the plurality of sections a driving voltage for generating the ultrasonic waves is increased in steps of increment voltages.

5. The apparatus of claim 1, further comprising treatment plan setting means for setting a plan of a procedure for the ultrasonic wave irradiation by the ultrasonic wave irradiation means in the entire ultrasonic wave medical treatment process, and wherein the control means controls the ultrasonic wave irradiation means according to the plan.

6. The apparatus of claim 5, further comprising means for displaying a graphic representation of the plan along with an indication of a progress of the entire ultrasonic wave medical treatment process.

7. A method of ultrasonic wave medical treatment, comprising the step of:

dividing an entire ultrasonic wave medical treatment process into a plurality of sections;

setting a total number of ultrasonic wave irradiations for the entire ultrasonic wave medical treatment process and a sectional number of ultrasonic wave irradiations for each of the plurality of sections;

irradiating ultrasonic waves on a treatment target as many times as the total number of ultrasonic wave irradiations, such that the ultrasonic waves are irradiated as many times as the sectional number of ultrasonic wave irradiations for each of the plurality of sections and then the ultrasonic wave irradiation is paused before the ultrasonic wave irradiation for a subsequent one of the plurality of sections is executed; and notifying that the ultrasonic wave irradiation for each of the plurality of sections is completed by generating a notification sound when the ultrasonic waves are irradiated as many times as the sectional number of ultrasonic wave irradiations successively.

8. The method of claim 7, wherein the ultrasonic waves are irradiated in the form of shock waves.

9. The method of claim 7, wherein the ultrasonic waves are irradiated in the form of continuous ultrasonic waves.

10. The method of claim 7, further comprising the steps of controlling a driving voltage for generating the ultrasonic waves such that in the ultrasonic wave irradiation for each of the plurality of sections the driving voltage is increased in steps of increment voltages.

11. The method of claim 7, further comprising the steps of:

obtaining tomographic images of the treatment target; and memorizing the tomographic images obtained in a course of the entire ultrasonic wave medical treatment process.

12. The method of claim 11, further comprising the step of setting a plan of timings for memorizing the topographic images according to which the memorizing is controlled.

13. An ultrasonic wave medical treatment apparatus, comprising:

setting means for setting a total number of ultrasonic wave irradiations for an entire ultrasonic wave medical treatment process which is divided into a plurality of sections, and a sectional number of ultrasonic wave irradiations for each of the plurality of sections;

ultrasonic wave irradiation means for irradiating ultrasonic waves on a treatment target as many times as the total number of ultrasonic wave irradiations;

control means for controlling the ultrasonic wave irradiation means such that the ultrasonic waves are irradiated as many times as the sectional number of ultrasonic wave irradiations for each of the plurality of sections and then the ultrasonic wave irradiations are paused before the ultrasonic wave irradiation for a subsequent one of the plurality of sections is executed;

imaging means for obtaining tomographic images of the treatment target; and image memory means for recording the tomographic images obtained by the imaging means in the course of the entire ultrasonic wave medical treatment process.

14. The apparatus of claim 13, further comprising treatment plan setting means for setting a plan of timings for the recording by the image memory means, and wherein the control means also controls the image memory means according to the plan.

15. A method of ultrasonic wave medical treatment, comprising the steps of:

dividing an entire ultrasonic wave medical treatment process into a plurality sections;

setting a total number of ultrasonic wave irradiations for the entire ultrasonic wave medical treatment process and a sectional number of ultrasonic wave irradiations for each of the plurality of sections;

irradiating ultrasonic waves on a treatment target as many times as the total number of ultrasonic wave irradiations, such that the ultrasonic waves are irradiated as many times as the sectional number of ultrasonic wave irradiations for each of the plurality of sections and then the ultrasonic wave irradiations are paused before the ultrasonic wave irradiation for a subsequent one of the plurality of sections is executed;

obtaining tomographic images of the treatment target; and recording the tomographic images obtained in a course of the entire ultrasonic wave medical treatment process.

16. The method of claim 15, further comprising the step of setting a plan of timings for the recording of the tomographic images according to which the recording is controlled.

* * * * *